US005130248A

United States Patent [19]

Kniskern et al.

[11] Patent Number: 5,130,248

[45] Date of Patent: Jul. 14, 1992

[54] EXPRESSION OF FUSION PROTEIN OF HIV ENVELOPE AND HBSAG

[75] Inventors: Peter J. Kniskern; Arpi Hagopian; Pamela Burke, all of Lansdale, Pa.

[73] Assignee: Merck & Co., Inc., Rahway, N.J.

[21] Appl. No.: 409,190

[22] Filed: Sep. 19, 1989

[51] Int. Cl.[5] .......................... C12N 5/06; C12N 5/19; C12P 21/06; C07H 21/04

[52] U.S. Cl. .............................. 435/240.2; 435/172.3; 435/69.1; 435/69.3; 435/320.1; 435/255; 536/27; 935/10; 935/22

[58] Field of Search ............. 536/27; 435/172.3, 69.9, 435/240.2, 320.1, 255, 256

[56] References Cited

FOREIGN PATENT DOCUMENTS 0278940 8/1988 European Pat. Off. .
0322394 6/1989 European Pat. Off. .

OTHER PUBLICATIONS

S. Matsushita et al. (1988) Journal of Virology 62:2107-2114.
D. M. Barnes (1988) Science 240:719-721.
M. R. Hilleman (1988) Vaccine 6:175-179.
K. Javaherian et al. (1989) Proc. Natl. Acad. Sci. USA 86:6768-6772.
C. Gurgo et al. (1988) Virology 164:531-536.
T. J. Palker et al. (1988) Proc. Natl. Acad. Sci. USA 85:1932-1936.
J. R. Rusche et al. (1988) Proc. Natl. Acad. Sci. USA 85:3198-3202.
T. J. Palker et al. (1989) Journal of Immunology 142:3612-3619.
Ratner, L. et al., "Human T-Lymphotropic Retroviruses," in O'Brien, S. J. (ed). *Genetic Maps* 1987 Cold Spring Harbor 1987, pp. 124-129.
Franchini, G. et al. Nature 328, 539 (1987).
Varmus, H. Genes & Dev. 2, 1055 (1988).
Goudsmit, J. et al., Proc. Nat. Acad. Sci. 85, 4478 (1988).
Ho. D. D. et al., J. Virol. 61, 2024 (1987).
Palker, T. J. et al., Proc. Natl. Acad. Sci. 85, 1932 (1988).
Skinner, M. A. et al., J. Virol. 62, 4195 (1988).
Berman, P. W. et al., Proc. Natl. Acad. Sci. 85, 5200 (1988).
Hu, S. L. et al., Nature 328, 721 (1987).
Lasky, L. A. et al., Science 233, 209 (1986).
Putney, S. et al., Science 234, 1392 (1986).
Robey, W. G. et al., Proc. Natl. Acad. Sci. 83, 7023.
Rusche, J. R. et al., Proc. Natl. Acad. Sci. 84, 6924 (1987) (Rusche II).
Genetic Engineering News, Jan. 1988, vol. 8, p. 23.
Hruska, J. F. et al., J. Virol. 21, 666 (1977).
Valenzuela, P. et al., 3 (4), 317 (1985).
Zoller, M. J. et al., Nucl. Acids. Res. 10, 6487 (1982).
Russell, D. W. et al., J. Biol. Chem., 258, 2674 (1983).
Kniskern, P. J. et al., Gene 46, 135 (1986) (Kniskern I).
Ellis, R. W. et al., Viral Hepatitis and Liver Disease, Alan R. Liss, Inc., pp. 1079-1086, 1988.
Carty, C. et al., J. Ind. Microbio. 2, 117 (1987).
Kniskern, P. et al., Hepatology 8, 82 (1988) (Kniskern II).
Wampler, D. E. et al., in Chanock, R. M. et al. (eds.) "Modern Approaches to Vaccines," Cold Spring Harbor 1984, pp. 251-256.
Robertson, G. A. et al., J. Virol. Meth. 20, 195 (1988).
Michel, M-L. et al., Proc. Natl. Acad. Sci. 85, 7957 (1988).
Adams, S. E. et al., Nature 329, 68 (1987).
Neurath, A. R. et al. Molecular Imm. 26, 53 (1989).
Delpeyroux, F. et al., J. Mol. Biol. 195, 343 (1987).
Standring, D. N. et al., Proc. Natl. Acad. Sci. 83, 9338 (1986).
Ono, Y. et al., Nucl. Acads. Res. 11, 1747 (1983).
Fujiyama, A. et al. Nucl. Acids Res. 11, 4601 (1983).

*Primary Examiner*—Richard A. Schwartz
*Assistant Examiner*—Johnny F. Railey, II
*Attorney, Agent, or Firm*—Roy D. Meredith; Charles M. Caruso

[57] ABSTRACT

The present invention relates to recombinant fusion polypeptides of HIV envelope and HBsAg, suitable as vaccines against AIDS and/or ARC and hepatitis, as well as immunogens for inducing antibodies for passive protection or treatment of AIDS and/or ARC.

4 Claims, No Drawings

EXPRESSION OF FUSION PROTEIN OF HIV ENVELOPE AND HBSAG

BACKGROUND OF THE INVENTION

Acquired Immune Deficiency Syndrome (AIDS) is the clinical manifestation of the apparent infection of CD4 helper T-cells and other cell targets by human immunodeficiency virus (HIV), also previously referred to as human T-lymphotropic virus type III (HTLV-III), Lymphoadenopathy-associated virus (LAV), or AIDS-related virus (ARV) (hereinafter collectively "HIV"). AIDS is a transmissible deficiency of cellular immunity characterized by opportunistic infections and certain malignancies. A similar disease, AIDS-related complex (ARC), shares many of the epidemiological features and immune abnormalities with AIDS, and often precedes the clinical manifestations of AIDS.

A vaccine against AIDS and/or ARC is an ideal prophylactic treatment for preventing the delibilitating effects of infection by HIV. Applicants have discovered an ummunogen useful for such a vaccine. The immunogen is a 5'fusion of the HBsAg (Hepatitis B surface antigen) and one or more HIV envelope fragments.

Many of the details of the genetic function and virion struction of HIV have not yet been elucidated. However, certain general features have emerged. An RNA virus with a genome titaling about 9 kilobases (kb), the nucleotide sequence of HIV contains seven major open reading frames (ORFs) corresponding to the gag, pol and env, vif, tat, rev, and nef genes. The genes gag, pol and env code respectively for core subunits, viral enzymes such as reverse transcriptase or pretease, and outer surface (envelope) subunits. The gene vif codes for a viral infectivity factor, which is a protein involved with enhancement of cell-to-cell transmission of virions without affecting the budding process. The gene tat codes for a small protein required for viral infectivity, but its mechanism of action is not clear. The gene rev regulates expression of the viral proteins of gag, pol and env genes, possibly by facilitating transport of incompletely spliced RNA. The nef gene codes for a viral protein found in the cell cytoplasm, and it may modulate the host cellular signaling system and server as a transcriptional silencer. Terminal repeats in the nucleotide sequence are common to many retroviruses such as HIV and are required for viral repliction and integration into the host chromosome. More recent discussions of the general nature of HIV genomic structure, replication and regulation are found in Ratner, L. et al. "Human T-Lymphotropic Retroviruses," in O'Brien, S. J. (ed.) *Genetic Maps* 1987 Cold Spring Harbor 1987 pp. 124–129; Franchini, G. et al., Nature 328, 539 (1987); Varmus, H. Genes & Dev 2, 1055 (1988).

Attempts to develop a vaccine to prevent infection with HIV generally have concentrated on the elicitation of specific virus-neutralizing antibodies. A region of the HIV surface coat protein (gp120) which is involved in the generation of such antibodies has been defined [Goudsmit et al., Proc. Natl. Acad. Sci. U.S.A. 85, 4478 (1988); Ho et al., J. Virol. 61, 2024 (1987); Matsushita et al., J. Virol. 62, 2107 (1988); Palker et al., Proc. Natl. Acad. Sci. U.S.A. 85, 1932 (1988); Rusche et al., Proc. Natl. Acad. Sci. U.S.A. 85, 3198 (1988); Skinner et al., J. Virol. 62, 4195 (1988)]. However, attempts to use the intact viral coat protein or portions thereof to readily elicit significant levels of neutralizing antibodies have proven unsuccessful [Berman et al., Proc. Natl. Acad. Sci. U.S.A. 85, 5200 (1988); Hu et al., Nature 328, 721 (1987); Lasky et al., Science 233, 209 (1986); Putney et al., Science 234, 1392 (1986); Robey et al., Proc. Natl. Acad. Sci. U.S.A. 83, 7023 (1986); Rusch et al., Proc. Natl. Acad. Sci. U.S.A. 84, 6924 (1987)].

Applicants of the present invention have constructed novel vectors for the synthesis of novel recombinant fusion protein (RFP) wherein the RFP is an amino-terminal fusion of HIV envelope protein fragment sequence with HBsAg at the carboxy-terminal end. The fusions of the present invention are capable of exhibiting a neutralizing antibody response, which is thought to be a critical requirement of vaccine efficacy. The RFP's of the present invention are useful as vaccines against AIDS and/or ARC, as well as against hepatitis.

The present applicaiton is drawn to genes for novel RFP's, their clonging and expression vectors, expression systems for RFP, as well as processes for making these constructions and for purifying the resulting RFP. The present application also encompasses formulations of RFP suitable as vaccines against AIDS and/or ARC, as well as hepatitis, whether or not in combination with other AIDS antivirals, immunomodulators, antibiotics or vaccines. Such an invention provides an immunogen useful for inducing antibodies for passive protection or treatment of AIDS and/or ARC. The immunogen and its specific antibodies are useful diagnostic reagents.

One advantage of the RFP of the present invention is that it provides a vaccine for simultaneous protection against hepatitis and AIDS. The particular heptatitis disease indicated here are those caused by hepatitis B virus (HBV).

AIDS is a disease caused by a virus (HIV) with a unique collection of attributes. HIV itself targets the immune system; it possesses a reverse transcriptase capable of turning out highly mutated progeny; it is sequestered from the immune system and it has a hypervariable surface in the env region. See, e.g. Hilleman, M. R., Vaccine 6, 175 (1988); Barnes, D. M., Science 240, 719 (1988). In view of these attributes, it was neither anticipated nor expected that the fusions of this invention would be useful as AIDS vaccines.

BRIEF DESCRIPTION OF THE INVENTION

The present invention encompasses recombinant fusion polypeptides (RFP's) wherein RFP is an amino-terminal fusion of HIV envelope protein fragment with Hepatitis B surface antigen (HBsAg) at the carboxy-terminal end. Formulations of RFP are suitable as vaccines against AIDS and/or ARC, as well as hepatitis, whether or not in combination with other AIDS antivirals, immunomodulators, antibiotics or vaccines. The present invention also provides the RFP as an immunogen useful for inducing antibodies for passive protection or treatment of AIDS and/or ARC. Furthermore, the immunogen and its specific antibodies are useful diagnostic reagents.

ABBREVIATIONS AND DEFINITIONS

| | |
|---|---|
| AIDS | Acquired immune deficiency syndrome |
| ARC | AIDS-related complex |
| HIV | Generic term for the presumed etiological agent of AIDS and/or ARC, also referred to as strains HTLV-III, LAV, and ARV. |

-continued

| | |
|---|---|
| Recombinant fusion polypeptide (RFP) | A polypeptide or oligopeptide expressed as a contiguous translation product from a spliced foreign DNA in a recombinant eukaryotic or procaryotic expression system, wherein the spliced foreign DNA is derived from 2 or more coding sequences of different origin, and ligated together. |
| Recombinant protein | A polypeptide or oligopeptide expressed by foreign DNA in a recombinant eukaryotic or procaryotic expression system. |
| Recombinant expression system | A cell line, explant, organ, or organism including animals or plants, containing a foreign DNA expressing a foreign protein or a foreign polypeptide. |

Amino Acids

| Full Name | Three-letter symbol |
|---|---|
| Alanine | Ala |
| Arginine | Arg |
| Asparagine | Asn |
| Aspartic acid | Asp |
| Asn and/or Asp | Asx |
| Cysteine | Cys |
| Glutamine | Gln |
| Glutamic acid | Glu |
| Gln and/or Glu | Glx |
| Glycine | Gly |
| Histidine | His |
| Isoleucine | Ile |
| Leucine | Leu |
| Lysine | Lys |
| Methionine | Met or MET |
| Phenylalanine | Phe |
| Proline | Pro |
| Serine | Ser |
| Threonine | Thr |
| Tryptophan | Trp |
| Tyrosine | Tyr |
| Valine | Val |

The terms "protein," "peptide," "oligopeptide," and "polypeptide" and their plurals have been used interchangeably to refer to chemical compounds having amino acid sequences of five or more amino acids. "Amino acid" refers to any of the 20 common amino acids for which codons are naturally available, and are listed in the table of amino acids given below.

DETAILED DESCRIPTION OF THE INVENTION

The present invention provides an effective vaccine against AIDS or ARC, and comprises an antigenic RFP of the following amino acid sequences.

RP135/HBsAg

| | | | | | | | | | | | | | | | | | |
|---|---|---|---|---|---|---|---|---|---|---|---|---|---|---|---|---|---|
| | | | | | | | | 48 | | | | | | | | | 75 |
| ATG | AAC | AAT | ACG | CGT | AAA | AGT | ATC | CGT | ATC | CAG | AGA | GGG | CCC | GGG | AGA | GCA | TTT |
| MET | Asn | Asn | Thr | Arg | Lys | Ser | Ile | Arg | Ile | Gln | Arg | Gly | Pro | Gly | Arg | Ala | Phe |
| | | | | | | | | 102 | | | | | | | | | 129 |
| GTT | ACA | ATA | GGA | AAA | ATA | GGA | ATG | GAG | AAC | ATC | ACA | TCA | GGA | TTC | CTA | GGA | CCC |
| Val | Thr | Ile | Gly | Lys | Ile | Gly | MET | Glu | Asn | Ile | Thr | Ser | Gly | Phe | Leu | Gly | Pro |
| | | | | | | | | 156 | | | | | | | | | 183 |
| CTG | CTC | GTG | TTA | CAG | GCG | GGG | TTT | TTC | TTG | TTG | ACA | AGA | ATC | CTC | ACA | ATA | CCG |
| Leu | Leu | Val | Leu | Gln | Ala | Gly | Phe | Phe | Leu | Leu | Thr | Arg | Ile | Leu | Thr | Ile | Pro |
| | | | | | | | | 210 | | | | | | | | | 237 |
| CAG | AGT | CTA | GAC | TCG | TGG | TGG | ACT | TCT | CTC | AAT | TTT | CTA | GGG | GGA | TCT | CCC | GTG |
| Gln | Ser | Leu | Asp | Ser | Trp | Trp | Thr | Ser | Leu | Asn | Phe | Leu | Gly | Gly | Ser | Pro | Val |
| | | | | | | | | 264 | | | | | | | | | 291 |
| TGT | CTT | GGC | CAA | AAT | TCG | CAG | TCC | CCA | ACC | TCC | AAT | CAC | TCA | CCA | ACC | TCC | TGT |
| Cys | Leu | Gly | Gln | Asn | Ser | Gln | Ser | Pro | Thr | Ser | Asn | His | Ser | Pro | Thr | Ser | Cys |
| | | | | | | | | 318 | | | | | | | | | 345 |
| CCT | CCA | ATT | TGT | CCT | GGT | TAT | CGC | TGG | ATG | TGT | CTG | CGG | CGT | TTT | ATC | ATA | TTC |
| Pro | Pro | Ile | Cys | Pro | Gly | Tyr | Arg | Trp | MET | Cys | Leu | Arg | Arg | Phe | Ile | Ile | Phe |
| | | | | | | | | 372 | | | | | | | | | 399 |
| CTC | TTC | ATC | CTG | CTG | CTA | TGC | CTC | ATC | TTC | TTA | TTG | GTT | CTT | CTG | GAT | TAT | CAA |
| Leu | Phe | Ile | Leu | Leu | Leu | Cys | Leu | Ile | Phe | Leu | Leu | Val | Leu | Leu | Asp | Tyr | Gln |
| | | | | | | | | 426 | | | | | | | | | 453 |
| GGT | ATG | TTG | CCC | GTT | TGT | CCT | CTA | ATT | CCA | GGA | TCA | ACA | ACA | ACC | AGT | ACG | GGA |
| Gly | MET | Leu | Pro | Val | Cys | Pro | Leu | Ile | Pro | Gly | Ser | Thr | Thr | Thr | Ser | Thr | Gly |
| | | | | | | | | 480 | | | | | | | | | 507 |
| CCA | TGC | AAA | ACC | TGC | ACG | ACT | CCT | GCT | CAA | GGC | AAC | TCT | ATG | TTT | CCC | TCA | TGT |
| Pro | Cys | Lys | Thr | Cys | Thr | Thr | Pro | Ala | Gln | Gly | Asn | Ser | MET | Phe | Pro | Ser | Cys |
| | | | | | | | | 534 | | | | | | | | | 561 |
| TGC | TGT | ACA | AAA | CCT | ACG | GAT | GGA | AAT | TGC | ACC | TGT | ATT | CCC | ATC | CCA | TCG | TCC |
| Cys | Cys | Thr | Lys | Pro | Thr | Asp | Gly | Asn | Cys | Thr | Cys | Ile | Pro | Ile | Pro | Ser | Ser |
| | | | | | | | | 588 | | | | | | | | | 615 |
| TGG | GCT | TTC | GCA | AAA | TAC | CTA | TGG | GAG | TGG | GCC | TCA | GTC | CGT | TTC | TCT | TGG | CTC |
| Trp | Ala | Phe | Ala | Lys | Tyr | Leu | Trp | Glu | Trp | Ala | Ser | Val | Arg | Phe | Ser | Trp | Leu |

-continued

| | | | | | | | | | | | | | | | | | |
|---|---|---|---|---|---|---|---|---|---|---|---|---|---|---|---|---|---|
| | | | | | | | | 642 | | | | | | | | | 669 |
| AGT | TTA | CTA | GTG | CCA | TTT | GTT | CAG | TGG | TTC | GTA | GGG | CTT | TCC | CCC | ACT | GTT | TGG |
| Ser | Leu | Leu | Val | Pro | Phe | Val | Gln | Trp | Phe | Val | Gly | Leu | Ser | Pro | Thr | Val | Trp |
| | | | | | | | | 696 | | | | | | | | | 723 |
| CTT | TCA | GCT | ATA | TGG | ATG | ATG | TGG | TAT | TGG | GGG | CCA | AGT | CTG | TAC | AGC | ATC | GTG |
| Leu | Ser | Ala | Ile | Trp | MET | MET | Trp | Tyr | Trp | Gly | Pro | Ser | Leu | Tyr | Ser | Ile | Val |
| | | | | | | | | 750 | | | | | | | | | 777 |
| AGT | CCC | TTT | ATA | CCG | CTG | TTA | CCA | ATT | TTC | TTT | TGT | CTC | TGG | GTA | TAC | ATT | TAA |
| Ser | Pro | Phe | Ile | Pro | Leu | Leu | Pro | Ile | Phe | Phe | Cys | Leu | Trp | Val | Tyr | Ile, | |

or variant thereof,
or pharmaceutically acceptable salt thereof;

RP142/HBsAg

| | | | | | | | | | | | | | | | | | |
|---|---|---|---|---|---|---|---|---|---|---|---|---|---|---|---|---|---|
| | | | | | | | | 48 | | | | | | | | | 75 |
| ATG | TAC | AAT | AAG | CGT | AAA | CGG | ATC | CAT | ATC | GGG | CCC | GGG | AGA | GCA | TTT | TAT | ACA |
| MET | Tyr | Asn | Lys | Arg | Lys | Arg | Ile | His | Ile | Gly | Pro | Gly | Arg | Ala | Phe | Tyr | Thr |
| | | | | | | | | 102 | | | | | | | | | 129 |
| ACA | AAA | AAT | ATT | ATA | GGA | ATG | GAG | AAC | ATC | ACA | TCA | GGA | TTC | CTA | GGA | CCC | CTG |
| Thr | Lys | Asn | Ile | Ile | Gly | MET | Glu | Asn | Ile | Thr | Ser | Gly | Phe | Leu | Gly | Pro | Leu |
| | | | | | | | | 156 | | | | | | | | | 183 |
| CTC | GTG | TTA | CAG | GCG | GGG | TTT | TTC | TTG | TTG | ACA | AGA | ATC | CTC | ACA | ATA | CCG | CAG |
| Leu | Val | Leu | Gln | Ala | Gly | Phe | Phe | Leu | Leu | Thr | Arg | Ile | Leu | Thr | Ile | Pro | Gln |
| | | | | | | | | 210 | | | | | | | | | 237 |
| AGT | CTA | GAC | TCG | TGG | TGG | ACT | TCT | CTC | AAT | TTT | CTA | GGG | GGA | TCT | CCC | GTG | TGT |
| Ser | Leu | Asp | Ser | Trp | Trp | Thr | Ser | Leu | Asn | Phe | Leu | Gly | Gly | Ser | Pro | Val | Cys |
| | | | | | | | | 264 | | | | | | | | | 291 |
| CTT | GGC | CAA | AAT | TCG | CAG | TCC | CCA | ACC | TCC | AAT | CAC | TCA | CCA | ACC | TCC | TGT | CCT |
| Leu | Gly | Gln | Asn | Ser | Gln | Ser | Pro | Thr | Ser | Asn | His | Ser | Pro | Thr | Ser | Cys | Pro |
| | | | | | | | | 318 | | | | | | | | | 345 |
| CCA | ATT | TGT | CCT | GGT | TAT | CGC | TGG | ATG | TGT | CTG | CGG | CGT | TTT | ATC | ATA | TTC | CTC |
| Pro | Ile | Cys | Pro | Gly | Tyr | Arg | Trp | MET | Cys | Leu | Arg | Arg | Phe | Ile | Ile | Phe | Leu |
| | | | | | | | | 372 | | | | | | | | | 399 |
| TTC | ATC | CTG | CTG | CTA | TGC | CTC | ATC | TTC | TTA | TTG | GTT | CTT | CTG | GAT | TAT | CAA | GGT |
| Phe | Ile | Leu | Leu | Leu | Cys | Leu | Ile | Phe | Leu | Leu | Val | Leu | Leu | Asp | Tyr | Gln | Gly |
| | | | | | | | | 426 | | | | | | | | | 453 |
| ATG | TTG | CCC | GTT | TGT | CCT | CTA | ATT | CCA | GGA | TCA | ACA | ACA | ACC | AGT | ACG | GGA | CCA |
| MET | Leu | Pro | Val | Cys | Pro | Leu | Ile | Pro | Gly | Ser | Thr | Thr | Thr | Ser | Thr | Gly | Pro |
| | | | | | | | | 480 | | | | | | | | | 507 |
| TGC | AAA | ACC | TGC | ACG | ACT | CCT | GCT | CAA | GGC | AAC | TCT | ATG | TTT | CCC | TCA | TGT | TGC |
| Cys | Lys | Thr | Cys | Thr | Thr | Pro | Ala | Gln | Gly | Asn | Ser | MET | Phe | Pro | Ser | Cys | Cys |
| | | | | | | | | 534 | | | | | | | | | 561 |
| TGT | ACA | AAA | CCT | ACG | GAT | GGA | AAT | TGC | ACC | TGT | ATT | CCC | ATC | CCA | TCG | TCC | TGG |
| Cys | Thr | Lys | Pro | Thr | Asp | Gly | Asn | Cys | Thr | Cys | Ile | Pro | Ile | Pro | Ser | Ser | Trp |
| | | | | | | | | 588 | | | | | | | | | 615 |
| GCT | TTC | GCA | AAA | TAC | CTA | TGG | GAG | TGG | GCC | TCA | GTC | CGT | TTC | TCT | TGG | CTC | AGT |
| Ala | Phe | Ala | Lys | Tyr | Leu | Trp | Glu | Trp | Ala | Ser | Val | Arg | Phe | Ser | Trp | Leu | Ser |
| | | | | | | | | 642 | | | | | | | | | 669 |
| TTA | CTA | GTG | CCA | TTT | GTT | CAG | TGG | TTC | GTA | GGG | CTT | TCC | CCC | ACT | GTT | TGG | CTT |
| Leu | Leu | Val | Pro | Phe | Val | Gln | Trp | Phe | Val | Gly | Leu | Ser | Pro | Thr | Val | Trp | Leu |
| | | | | | | | | 696 | | | | | | | | | 723 |
| TCA | GCT | ATA | TGG | ATG | ATG | TGG | TAT | TGG | GGG | CCA | AGT | CTG | TAC | AGC | ATC | GTG | AGT |
| Ser | Ala | Ile | Trp | MET | MET | Trp | Tyr | Trp | Gly | Pro | Ser | Leu | Tyr | Ser | Ile | Val | Ser |
| | | | | | | | | 750 | | | | | | | | | |
| CCC | TTT | ATA | CCG | CTG | TTA | CCA | ATT | TTC | TTT | TGT | CTC | TGG | GTA | TAC | ATT | TAA | |
| Pro | Phe | Ile | Pro | Leu | Leu | Pro | Ile | Phe | Phe | Cys | Leu | Trp | Val | Tyr | Ile, | | |

or variant therof,
or pharmaceutically acceptable salt thereof.

Construction of Recombinant Fusion Polypeptides Formed From HIV and Hepatitis B Fragments The fusion polypeptide of the present invention is provided for immunological purposes. It serves as a novel and useful antigen in the treatment or prevention of AIDS or ARC. It is the prinicipal constituent of an AIDS vaccine, to be used either actively or passively and either pre- or post-exposure to prevent or treat HIV infection or disease.

A. Preparation of Spliced Foreign DNA Inserts

Following well known and conventional practice, coding sequences are prepared by ligation of other sequences, cloning, mutagenesis, organic synthesis, or combination thereof, in accordance with the principles and practice of constructing DNA sequences.

B. Expressions of Recombinant Fusion Polypeptides in a Recombinant Expression System It is now a relativelyy straightforward technology to prepare cells expressing a foreign gene. Such cells act as hosts and may include, for the RFP's of the present invention, yeasts, fungi, insect cells, plants cells or animals cells. Expression vectors for many of these host cells have been isolated and characterized, and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extrachromosomal plasmids or after integration in whole or in part in the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector, and other factors readily appreciated by those of ordinary skill in the art.

The foreign DNA insert of interest comprises any DNA sequence coding for RFP including any synthetic sequence with this coding capacity or any such cloned sequennce or combination thereof. For example, RFP coded and expressed by an entirely recombinant DNA sequence is encompassed by this invention but not to the exclusion of RFP peptides obtained by other techniques.

Vectors useful for constructing eukaryotic expression systems for the production of RFP comprise the RFP DNA sequence, operatively linked thereto with appropriate transcriptional activation DNA sequences, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

Yeast expression systems, which are the preferred variety of recombinant eukaryotic expression system, generally employ *Saccharomyces cerevisiae* as the species of choice for expressing recombinant proteins.

Other species of the genus Saccharomyces are suitable for recombinant yeast expression system, and include but are not limited to carlsbergensis, uvarum, rouxii, montanus, kluyveri, elongisporus, norbensis, oviformis, and diastaticus.

*S. cerevisiae* and similar yeasts possess well known promoters useful in the construction of expression systems active in yeast, including but not limited to GAP, GAL10, ADH2, PHO5, and alpha mating factor.

Yeast vectors useful for constructing recombinant yeast expression systems for expressing RFP include, but are not limited to, shuttle vectors, cosmid plasmids, chimeric plasmids, and those having sequences derived from 2-micron circle plasmids.

Insertion of the appropriate DNA sequence coding for RFP into these vectors will, in principle, result in a useful recombinant yeast expression system for RFP where the modified vector is inserted into the appropriate host cell, by transformation or other means.

Recombinant mammalian expression system are another means of producing the RFP for the vaccines/immunogens of this invention. In general, a host mammalian cell can be any cell that has been efficiently cloned in cell culture. However, it is apparent to those skilled in the art that mammalian expression options can be extended to include organ culture and transgenic animals. Host mammalian cells useful for the purpose of constructing a recombinant mammalian expression system include, but are not limited to, Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, D. M. (ed.) "DNA Cloning: A Practical Approach," IRLL 1985, Vols. I and II.

Recombinant insect expression systems provide a practical alternative means of producing the RFP for the vaccines/immunogens of this invention. Baculovirus is a typical vector for this system.

RFP's (recombinant fusion polypeptides) may possess additional and desirable structural modifications not shared with the same organically synthesized peptide, such as adenylation, carboxylation, glycosylation, hydroxylation, methylation, phosphorylation or myristylation. These added features may be chosenn or preferred as the case may be, by the appropriate choice of recombinant expression system. On the other hand, RFP may have its sequence extended by the principles and practice of organic synthesis.

VACCINE FORMULATION

Ann immunological vector, carrier or adjuvant may be added as an immunological vehicle to the antigen according to conventional immunological testing or practice.

Adjuvants may or may not be added during the preparation of the vaccines of this invention. Alum is a typical and preferred adjuvant in human vaccines, especially in the form of a thixotropic, viscous, and homogeneous aluminum hydroxide gel. For example, one embodiment of the present invention is the prophylactic vaccination of patients with a suspension of alum adjuvant as vehicle and RFP as the selected immunogen or antigen.

The vaccines/immunogens of this invention may also be administered to healthy individuals and/or animal species in order to prepare polyclonal antibodies and/or hybridoma cell lines or transgenic animals expressing immunoglobulins which may be used as passive prophalaxis or therapy or as diagnostic reagents.

The vaccines of this invention may be effectively administered, whether at periods of pre-exposire and/or post-exposure, in combination with effective amounts of the AIDS antivirals, immunomodulators, antibiotics, or vaccines of Table I [source: *Market Letter*, Nov. 30, 1987, p. 26-27; *Genetic Engineering News*, January 1988, Vol. 8, p. 23.]

TABLE I[1]

| Drug Name | Manufacturer | Indication |
|---|---|---|
| | A. Antivirals | |
| AL-721 | Ethigen | ARC, PGL |
| BETASERON (interferon beta) | Triton Biosciences | AIDS, ARC, KS |
| CARRISYN (polymannoacetate) | Carrington Labs | ARC |
| CYTOVENE (ganciclovir) | Syntex | CMV |
| DDC (dideoxycytidine) | Hoffmann-La Roche | AIDS, ARC |
| FOSCARNET (trisodium phosphonoformate) | Astra AB | HIV inf, CMV retinitis |
| HPA-23 | Rhone-Poulenc Sante | HIV infection |
| ORNIDYL (eflornithine) | Merrell Dow | PCP |
| PEPTIDE T (octapeptide sequence) | Peninsula Labs | AIDS |
| RETICULOSE (nucleophospho-protein) | Advanced Viral Research | AIDS, ARC |
| IR (zidovudine; AZT) | Burroughs Wellcome | AIDS, advanced ARC pediatric AIDS, KS, asympt HIV, less severe HIV, neurological involvement. |
| RIFABUTIN (ansamycin LM 427) | Adria Labs | ARC |
| (trimetrexate) | Warner-Lambert | PCP |
| UA001 | Ueno Fine Chem Industry | AIDS, ARC |
| VIRAZOLE (ribavirin) | Viratek/ICN | AIDS, ARC, KS |
| WELLFERON (alfa interferon) | Burroughs Wellcome | KS, HIV, in comb with RETROVIR |
| ZOVIRAX (acyclovir) | Burroughs Wellcome | AIDS, ARC, in comb with RETROVIR |
| | B. Immunomodulators | |
| ABPP (bropirimine) | Upjohn | Advanced AIDS, KS |
| AMPLIGEN (mismatched RNA) | DuPont HEM Research | ARC, PGL |
| (Anti-human alpha interferon antibody) | Advanced Biotherapy Concepts | AIDS, ARC, KS |
| Colony Stimulating Factor (GM-CSF) | Sandoz Genetics Institute | AIDS, ARC, HIV, KS |
| CL246,738 (CL246,738) | American Cynamid | AIDS |
| IMREG-1 | Imreg | AIDS, ARC, PGL, KS |
| IMREG-2 | Imreg | AIDS, ARC, PGL, KS |
| IMUTHIOL (diethyl dithio carbamate) | Merieux Institute | AIDS, ARC |
| IL-2 (interleukin-2) | Cetus | AIDS, KS |
| IL-2 (interleukin-2) | Hoffmann-La Roche Immunex | AIDS, KS |
| INTRON-A (interferon alfa) | Schering-Plough | KS |
| ISOPRINOSINE (inosine pranobex) | Newport Pharmaceuticals | ARC, PGL, HIV seropositive patients |
| (methionine enkephalin) | TNI Pharmaceuticals | AIDS, ARC |
| MTP-PE (muramyl-tripep-tide) | Ciba-Geigy | KS |
| THYMOPENTIN (TP-5) (thymic compound) | Ortho Pharmaceuticals | HIV infection |
| ROFERON (interferon alfa) | Hoffmann-La Roche | KS |
| (recombinant erythropoietin) | Ortho Pharmaceuticals | severe anemia assoc with AIDS |

TABLE I[1]-continued

| Drug Name | Manufacturer | Indication |
|---|---|---|
| | | & RETROVIR therapy |
| TREXAN (naltrexone) | DuPont | AIDS, ARC |
| TNF (tumor combination necrosis factor) | Genentech | ARC, in interferon gamma |
| | C. Antibiotics | |
| PENTAM 300 (pentamidine isethionate) | LyphoMed | PCP |
| | D. Vaccines | |
| Gag | Merck | AIDS, ARC |
| RP135-Omp conjugate | Merck | AIDS, ARC |

[1]Abbreviations: AIDS (Acquired Immune Deficiency Syndrome); ARC (AIDS related complex); CMV (Cytomegalovirus, which causes an opportunistic infection resulting in blindness or death in AIDS patients); HIV (Human Immunodeficiency Virus, previously known as LAV, HTLV-III or ARV); KS (Kaposi's sarcoma); PCP (Pneumonocystis carinii pneumonia, an opportunistic infection); PGL (persistent generalized lymphadenopathy).

It will be understood that the scope of combinations of the vaccines of this invention (either actively or passively administered) with AIDS antivirals, immunoglobulins, immunomodulators, antibiotics or vaccines is not limited to the list in the above Table, but includes in principle any combination with any pharmaceutical composition useful for the treatment of AIDS. The AIDS or HIV vaccines of this invention include vaccines to be used pre- or post-exposure to prevent or treat HIV infection or disease, and are capable of producing an immune response specific for the immunoge. It will also be understood that the choice of HBsAg, as part of the RFP, extends the scope of this invention to prevention of diseases caused by HBV, delta virus and other agents for which HBsAg induces a beneficial immune response..

EXAMPLE I

Cloning of HBV DNA in pBR322

HBV Dane particles (serotype adw) were isolated and purified from human plasma (carrier), and double-stranded DNA was synthesized by the endogenous polymerase in the Dane particles according to the methods of Landers et al., [*J. Virology*, 23, 368–376, (1977)] and Hruska et al., [*J. Virology*, 21, (1977)]. The DNA was isolated after digestion with 666 Proteinase K in SDS followed by extraction with phenol/chloroform and ethanol precipitaton. The HBV genomic DNA was digested with EcoRI, producing a single 3.2 kbp fragment, that was cloned into the EcoRI site of pBR322 to form pHBV/ADW-1. The presence of the HBV DNA was confirmed by EcoRI digestion, Southern blot transfer to nitrocellulose, and hybridization with [$^{32}$P-labelled] specific oligonucleotide probes.

EXAMPLE II

Construction of HBV preS2+S ORF in pUC18

The plasmid pHBV/ADW-1 (from Example I above) was digested with EcoRI and AccI and the 0.8 kbp fragment purified by preparative agarose gel electrophoresis.

To reconstruct the 5′ portion of the preS2+S open reading frame (ORF), a pair of oligonucleotides was synthesized which reconstituted the ORF from the EcoRI site upstream to the ATG through a 10 bp non-translated leader sequence through a HindIII site to an EcoRI terminus. The sequence of this oligonucleotide is:

```
AATTCAAGCTTACAAAACAAAATGCAGTGG
    GTTCGAATGTTTTGTTTTACGTCACCTTAA
```

To reconstruct the 3′ portion of the preS2+S-ORF, a second pair of oligonucleotides was synthesized which reconstituted the ORF from the AccI HindIII site to a BamHI terminus. The sequence of this oligonucleotide is:

```
ATACATTTAAAGCTTG
  TGTAAATTTCGAACCTAG
```

The 0.8 kbp fragment and the two synthetic oligonucleotide pairs were then ligated into pCU18 which had been previously digested with EcoRI and BamHI to create vector pUC18 preS2+S.

EXAMPLE III

Mutagenesis of HBV DNA

DNA sequence analysis of pUC18 preS2+S revealed 2 base substitutions which resulted in aa differences from the preS2+S sequence encoded by the DNA of pHBpreSGAP347/19T [Valenzuela et al., *Biotechnology*, 3(4), 317–320 (1985)]. In order to express identical polypeptides for both constructions, these nucleotide substitutions, which were T instead of C at base 64 of the 846 bp ORF of HBV preS2+S (encoding Phe rather than Leu) and C instead of A at base 352 (encoding His rather than Gln) were changed by site-directed mutagenesis [Zoller et al., *Nucleic Acids Research* 10:6487–6500 (1982)]. The encoded aa sequence for the optimized construction then was verified and cloned into pUC13 and pUC19 previously cut with HindIII or EcoRI and HindIII respectively to create the plasmids pUC13 preS2+S and pUC19 preS2+S. It is obvious to those skilled in the art that this invention is not limited to this sequence and extends to any sequence wherein the DNA encodes a polypeptide with HBV antigenicity.

EXAMPLE IV

Construction of HIV HGP30/HBsAg Fusion ORF

A pair of 148 bp oligonucleotides was synthesized which encode the 30 AA sequence of HGP30 with a 5′ EcoRI terminus through a HindIII site, a 10 bp nontranslated leader sequence, an ATG followed by the HGP30 ORF to a 3′ BamHI terminus. The sequence of this oligo pair is:

```
5' AATTCAAGCTTACAAAACAAAATGGTGCATCAA
       GTTCGAATGTTTTGTTTTACCACGTAGTT

AGGATAGAGATAAAAGACACCAAGGAGGCCTTA
TCCTATCTCTATTTTCTGTGGTTCCTCCGGAAT

GACAAGATAGAGGAAGAGCAAAACAAAAGTAAG
CTGTTCTATCTCCTTCTCGTTTTGTTTTCATTC

AAAAAAGCGCAGCAAATGGAGAACATCACATCAGGA
TTTTTTCGCGTCGTTTACCTCTTGTAGTGTAGTCCT

TTCCTAGGGCCCG 3'
AAGGATCCCGGGCCTAG
```

This pair of oligos was then ligated into pUC19 which had been previously digested with EcorRI and BamHI, to create the intermediate vector pUC19 HGP30.

The intermediate vector pUC19 HGP30 was then digested with AvrII and BamHI. To create the 3′ end of the ORF, a pair of synthetic oligonucleotides (16/18 bp) which codes from an AccI site through the translational terminator through a HindIII site to a BamHI terminus (as shown in Example II) was ligated with the vector at the BamHI site, the linear band was purified after agarose gel electropheresis. The 0.65 kbp StyI-AccI HBsAg DNA fragment (the source of which was the pUC19 preS2+S. from Example III) was ligated to the above vector to create the HIV HGP30/HBsAg fusion ORF. In this case StyI is compatible with the AvrII site. The correct DNA sequence was empirically verified.

EXAMPLE V

Construction of the HIV RP135/HBsAg Fusion ORF

The HIV HGP30/HBsAg vector from Example IV was digested with EcoRI and StyI, and the 3.35 kbp vector was purified after agarose gel electrophoresis.

A pair of 120 bp oligonucleotides were synthesized that comprised in their 5′ to 3′ order: an EcoRI terminus through a HindIII site, a 10 bp nontranslated leader sequence, an ATG, the RP135 ORF (Bases 901 and 973 of HIV envelope sequence of the BH10 serotype), the ATG of HBsAg to a StyI terminus. The sequence of this synthetic oligonucleotide is:

| | | | | | | | | | | | | | | | |
|---|---|---|---|---|---|---|---|---|---|---|---|---|---|---|---|
| AAT | TCA | AGC | TTA | CAA | AAC | AAA | ATG | AAC | AAT | ACG | CGT | AAA | AGT | ATC | |
| | GT | TCG | AAT | GTT | TTG | TTT | TAC | TTG | TTA | TGC | GCA | TTT | TCA | TAG | |
| | | | | | | | M | N | N | T | R | K | S | T | |
| CGT | ATC | CAG | AGA | GGG | CCC | GGG | AGA | GCA | TTT | GTT | ACA | ATA | GGA | AAA | |
| GCA | TAG | GTC | TCT | CCC | GGG | CCC | TCT | CGT | AAA | CAA | TGT | TAT | CCT | TTT | |
| R | I | Q | R | G | P | G | R | A | F | V | T | I | G | K | |
| ATA | GGA | ATG | GAG | AAC | ATC | ACA | TCA | GGA | TTC | | | | | | |
| TAT | CCT | TAC | CTC | TTG | TAG | TGT | AGT | CCT | AAG | GATC | | | | | |
| I | G | ... | | | | | | | | | | | | | |

This oligonucleotide pair was ligated to the 3.35 kbp linear DNA fragment purified as described above to create the plasmid designated HIVRP135/HBsAg, which codes for RP135/HBsAg.

EXAMPLE VI

Construction of the HIV RP142/HBsAg Fusion ORF

A pair of 117 bp oligonucleotides were synthesized that comprised in their 5′ to 3′ order: a 5′ EcoRI terminus, a 10 bp nontranslated leader sequence, an ATG, the RP142 ORF (Bases 916 to 985 of HBsAg to a StyI terminus. The sequence is this:

| | | | | | | | | | | | | | |
|---|---|---|---|---|---|---|---|---|---|---|---|---|---|
| AAT | TCA | AGC | TTA | CAA | AAC | AAA | ATG | TAC | AAT | AAG | CGT | AAA | |
| | GT | TCG | AAT | GTT | TTG | TTT | TAC | ATG | TTA | TTC | GCA | TTT | |
| | | | | | | | M | Y | N | K | R | K | |
| CGG | ATC | CAT | ATC | GGG | CCC | GGG | AGA | GCA | TTT | TAT | ACA | ACA | |
| GCC | TAG | GTA | TAG | CCC | GGG | CCC | TCT | CGT | AAA | ATA | TGT | TGT | |
| R | I | H | I | G | P | G | R | A | F | Y | T | T | |
| AAA | AAT | ATT | ATA | GGA | ATG | GAG | AAC | ATC | ACA | TCA | GGA | TTC | |
| TTT | TTA | TAA | TAT | CCT | TAC | CTC | TTG | TAG | TGT | AGT | CCT | AAG | GATC |
| ... | | | | | | | | | | | | | |

This oligomer pair was ligated to the vector HIV HGP30/HBsAg which had been previously digested with EcoRI and StyI from Example IV. The resulting plasmid was designated pUC19 HIVRP142/HBsAg, which codes for RP142/HBsAg.

EXAMPLE VII

Construction of the Regulatable Expression Cassette pADH2-tADH1

The pADH2Δ67(−1) *E. coli* clonging vector contains sequences which are capable in *S. cerevisiae* of driving expression of foreign genes inserted at a unique HindIII site from the AHD2 derepressible promoter [Russell et al., J. Biol. Chem. 258: 2674 (1983)]. The unique HindIII site is positioned between nucleotide −1 of the 5′ nontranslated flanking sequences and the transcriptional terminator of the ADH2 gene. pADH2Δ67(−1) was digested with BamHI and EcoRI, made flush-ended with the Klenow fragment of DNA polymerase I, and the 4.9 kbp fragment containing the ADH2 promoter and terminator was purified by preparative agarose gel electrophoresis. pUC7 was digested with PstI, made flush-ended with T4 DNA polymerase, and ligated to the 4.9 kbp ADH2fragment. The resulting plasmid was digested with SalI, and the 4.9 kbp fragment was purified by preparative agarose gel electrophoresis. pBR322 was digested with HindIII, made flush-ended with the Klenow fragment of DNA polymerase I, and self-ligated. The resulting plasmid was digested with SalI and ligated to the 4.9 kbp SalI fragment, creating the vector pBr322ΔHindIII-ADH2 (This vector served as the source of the ca. 1.25 kbp ADH2 promoter fragmennt).

The expression vector pGAP-tADH-2 has been described previously (Kniskern et al., (1986) *Gene*, 46, 134–141) and served as the source of the ca. 0.350 kbo ADH1 transcritional terminator fragment. The ADH1 terminator fragment was isolated by digestion with HindIII and SpHI and gel purified on agarose gel electrophoresis. It was ligated with pBr322 which had previously been digested with HindIII and SpHI. The resulting intermediate vector was used to isolate the ADH1 terminator by digesting with HindIII and SalI and gel purifying the 0.44 kbp piece. This was then ligated with the ca. 1.25 kbp HindIII-SalI ADH2 promoter fragment, and the resulting ca. 1.7 kbp pADH2-tADH1 cassette was gel isolated. The cassette was ligated with the SalI digested pBr322(ΔHindIII) vector (from above) creating the expression vector pBr322(ΔHindIII) pADH2-tADH1.

EXAMPLE VIII

Construction of HIV Peptide-HBsAg Fusion ORF in Expression Vector pADH2-tADH1

The fusion ORF's described in Examples V and VI above were removed from the pUC vectors by digestion with HindIII and isolated following agarose gel electrophoresis. These DNA fragments with HindIII termini were then ligated into vector pBr322(ΔHindIII) pADH2-tADH1 from Example VII which had been previously digested with HindIII; correct orientation was verified.

EXAMPLE IX

Construction of Yeast Shuttle Vectors

The resulting plasmids from Example VIII above were digested with SalI and the appropriate DNA fragment was isolated by agarose gel electrophoresis. The DNA fragment then was ligated into the unique SalI site of the pC1/1 creating the recombinant yeast shuttle vectors. This recombinant plasmid was used to transform *S. cerevisiae* strain CF42 (Ellis et al. Viral Hepatitis and Liver Disease, Alen R. Liss Inc. pp 1079–1086, 1988). Recombinant yeast clones were isolated and established as frozen stocks (Kniskern et al., Hepatology 8, 82–87, 1988).

EXAMPLE X

Growth And Expression Of Transformed Yeast Expressing HIV/HBsAg Fusion Proteins The clones from Example IX above were grown in synthetic selective (leu$^-$) medium [Carty, L. et al. J. Ind. Micorbio. 2, 117 (1987)] containing 2% glucose as a carbon source. Cells were grown for 16–24 hours at 30° C. to an $A^{600}$ of approximate 3–5, at which time larger flasks containing complex medium [Kniskern, P. et al. Hepatology 8, 82 (1988)] with 1.6% glucose as a carbon source were inoculated (inoculum size=10% vol/vol). Cells were grown for additional 45–48 hours to an $A^{600}$=12.0–14.0, during which time glucose depletion had derepressed the ADH2promoter. Expression of the desired antigen was verified by immunoblot reactivity. The immunoblots were developed and antisera reactive with either HBsAg or HIV. Both antisera reacted with the same polypeptide, the molecular size of which was in all cases identical to that predicted for the translational product of the fusion ORF.

EXAMPLE XI

Purification of HIV/HBsAg Fusion

Yeast cells were grown and harvested as described in Example X above. Harvested cells were frozen at −70° until use. Frozen cells expressing HIV/HBsAg polypeptides were thawed and resuspended in 0.1M HEPES buffer, pH 7.5 containing 10 mM ethylenediaminetetraacetic acid, 10 mM benzamidine-HCl, 10 mcg/mL pepstatin A, 25μ ME-64 and 0.13 trypsin inhibitor units/mL aprotinin. Immediately before breaking, phenylmethylsulfonylfluoride (200 mM in 2-propanol) was added to a final concentration of 2 mM and the cells were disrupted by passage three times through a pressure homogenizer at 20,000 psi yielding a yeast cell lysate. Triton X100 was added to a concentration of 0.256% and cell debris was removed by two-phase extraction between PEG 3350 and Dextran T500. The upper PEG phase containinig the antigen was recovered, and the antigen was isolated by immune-affinity chromatography as previously described [Wampler et al., In Chanock and Lerner (eds.): "Modern Approaches to Vaccines," Cold Spring Harbor, N.Y., Cold Springs Harbor Press, pp. 251–256 (1984)]. $NH_4SCN$ was removed by diafiltration against phosphate-buffered saline. Purified antigens were adsorbed to aluminum hydroxide for in vivo testing.

The immune-affinity purified product was a single component on silver-stained polyacrylamide gels, with an apparent molecular weight of approximately 28,000 daltons. Immunoblots with the appropriate antisera showed that the purified product bound both anti-HBsAg and anti-HIV-gp160. Immunoblots (to anti-HBsAg) of the cell lysate before and after addition of TX-100 showed two predominant bands at approximately 28,000 and 31,000 daltons present in approximately equal amounts. Numerous smaller molecular weight bands are also present in varying intensities. After the two-phase extraction the predominant band in the upper phase is the 28,000 dalton species. It appears that the two-phase extraction may be selective with the 28,000 dalton pepetide going to the upper phase and the 31,000 dalton peptide, along with the majority of lower molecular weight species, going to the lower phase. The immune-affinity purified product consists mainly of the 28,000 dalton peptide, a shadow of the 31,000 dalton species and very small amounts of lower molecular weight species.

It is apparent to those skilled in the art that isolation schema can also be used which enrich for the 31,000 species.

Examination by electron microscopy showed that HBsAg-like particles are present in very large number and aggregates of particles are also very prominant.

EXAMPLE XII

Protocol for Inoculation of Animals with the RP135/HBsAg Antigen

Alum was used as an adjuvant during the inoculation series. The inoculum was prepared by dissolving the RP135/HBsAg antigen in physiologic saline at a final antigen concentration of 100 μg/ml. Preformed alum (aluminum hydroxixde gel) was added to the solution to a final level of 500 μg/ml aluminum. The antigen was allowed to adsorb onto the alum gel for two hours at room temperature. Following adsorption, the gel with the antigen was washed twice which physiologic saline and resuspended in the saline to a protein concentration of 100 μg/ml.

African green monkeys were individually inoculated with four 100 mcg doses of the RP135HBsAg antigen adsorbed onto alum. Each dose was injected intramuscularly. The doses were delivered one or five months apart (week 0, 4, 8 and 28). The animals were bled at intervals of two or four weeks. Serum samples were prepared from each bleed to assay for the development of specific antibodies as described in the subsequent examples.

EXAMPLE XIII

Analysis of Sera for Anti-RP135 IgG Antibodies

Each serum sample was analyzed by enzyme-linked immunoadsorbent assay (ELISA). Polystyrene microtiter plates were coated with 0.5 μg per well of RP135 (as a free synthetic peptide) in phosphate-buffered physiological saline (PBS) at 4° C. Each well was then washed with PBS containing 0.5% TWEEN-20 (PBS-T). Test serum, diluted serially in PBS-T, was added to the peptide-containing wells and allowed to react with the adsorbed peptide for one hour at 36° C. After washing with PBS-T, alkaline phosphatase-conjugated goat anti-human IgG was added to the test wells and was allowed to react for one hour at 36° C. The wells were then washed extensively in PBS-T. Each well received 0.1% p-nitrophenyl phosphate in 10% diethanolamine, pH 9.8, containing 0.5 mM $MgCl_2 \bullet 6H_2O$. The ensuing reaction was allowed to proceed at room temperature for 30 minutes, at which time it was terminated by the addition of 3.0N NaOH.

The greater the interaction of antibodies in the test serum with the peptide substrate, the greater is the amount of alkaline phosphatase bound onto the well. The phosphotase enzyme mediates the breakdown of p-nitrophenyl phosphate into a molecular substance which absorbs light at a wavelength of 405 nm. Hence, there exists a direct relationship between the absorbence at 405 nm of light at the end of the ELISA reaction and the amount of peptide-bound antibody.

All the monkeys inoculated with the RP135/HBsAg antigen developed antibodies specifically capable of binding the RP135 peptide, as indicated by the anti-RP135 titers of Table II.

EXAMPLE XIV

Analysis of Sera for Activity which Specifically Neutralizes HIV Infectivity Virus-neutralizing activity was determined with an assay described by Robertson et al., J. Virol. Methods 20: 195-202 (1988). The assay measures specific HIV-neutralizing activity in test serum. The assay is based on the observation that MT-4 cells, a human T-lymbphoid cell line, are readily susceptible to infection with HIV and, afer a period of virus replication, are killed as a result of the infection.

The test serum was treated at 56° C. for 60 minutes prior to the assay. This treatment is required to eliminate non-specific inhibitors of HIV replication. Heat treated serum, serially diluted to RPMI-1640 cell culture medium was mixed with a standard infection dose of HIV. The dose had been determined prior to the assayy as containing the smallest quantity of virus required to kill all the MT-4 cells in the assay culture after a period of 7 days. The serum-virus mixture was allowed to interact for one hour at 37° C. It then was added to $1.0 \times 10^5$ MT-4 cells suspended in RPMI-1640 growth medium supplemented with 10% fetal bovine serum. The cultures were incubated at 37° C. in a 5% $CO_2$ atmosphere for 7 days.

At the end of the incubation period, a metabolic dye, DDT, was added to each culture. This dye is yellow in color upon visual inspection. In the presence of live cells, the dye is metabolically processed to a molecular species which yields a blue visual color. Neutralized HIV cannot replicate in the target MT-4 cells and therefore does not kill the cells. Hence, positive neutralization is assessed by the development of blue color following addition of the metabolic dye.

All the monkeys inoculated with the RP135/HBsAg antigen developed specific HIV infectivity-neutralizing activity, as indicated by the neutralizing activity titers of the Table II.

TABLE II

Evaluation of RP135/HBsAg-Inoculated Animals

| Animal # | Weeks, post-inoculation[1] | Anti-RP135 ELISA titer[2] | Neutralizing activity[3] |
|---|---|---|---|
| 63 | 0 | <20 | <10 |
| | 2 | <20 | <10 |
| | 4 | <20 | <10 |
| | 6 | 100 | 80 |
| | 8 | 100 | 40 |
| | 10 | 100 | 40 |
| | 12 | 20 | 80 |
| | 16 | 20 | 10 |
| | 20 | <20 | <10 |
| | 24 | <20 | <10 |
| | 28 | <20 | <10 |
| | 30 | 100 | 320 |
| | 32 | 20 | 80 |
| 89 | 0 | <20 | <10 |
| | 2 | <20 | <10 |
| | 4 | <20 | <10 |
| | 6 | 100 | 80 |
| | 8 | 500 | 160 |
| | 10 | 500 | 160 |
| | 12 | 100 | 160 |
| | 16 | 20 | 40 |
| | 20 | 20 | <10 |
| | 24 | 20 | <10 |
| | 28 | <20 | <10 |
| | 30 | 100 | 320 |
| | 32 | 20 | 40 |
| 97 | 0 | <20 | <10 |
| | 2 | <20 | <10 |
| | 4 | <20 | <10 |
| | 6 | 500 | 40 |
| | 8 | 100 | 20 |
| | 10 | 100 | 40 |
| | 12 | <20 | 10 |
| | 16 | <20 | <10 |
| | 20 | <20 | <10 |
| | 24 | <20 | <10 |
| | 28 | <20 | <10 |
| | 30 | 20 | 160 |

TABLE II-continued

| Evaluation of RP135/HBsAg-Inoculated Animals | | | |
|---|---|---|---|
| Animal # | Weeks, post-inoculation[1] | Anti-RP135 ELISA titer[2] | Neutralizing activity[3] |
| | 32 | 20 | 80 |

Footnotes to Table II:
[1]Each animal was inoculated with 100 μg of the antigen, alum-adsorbed, per dose. Doses were delivered intramuscularly at 0, 4, 8 and 28 weeks.
[2]Reciprocal of end-point ELISA titer using the RP135 synthetic peptide as substrate coating on microtiter plates.
[3]Reciprocal of end-point virus-neutralization titer.

While the foregoiing specification teaches the principles of the present invention, with examples provided for the purposes of illustration, it will be understood that the practice of the invention encompasses all the usual variations, adaptations, or modifications, as come within the scope of the following claims and its equivalents.

What is claimed is:

1. The gene coding for RP142/HBsAg.

2. A vector containing the gene coding for RP142/HBsAg.

3. A eukaryotic expression system for the synthesis of RP142/HBsAg in cells in vitro.

4. A yeast expression system for the synthesis of RP142/HBsAg.

* * * * *